United States Patent [19]
Woollam et al.

[11] Patent Number: 5,373,359
[45] Date of Patent: Dec. 13, 1994

[54] ELLIPSOMETER

[75] Inventors: John A. Woollam; Blaine D. Johs; David W. Doerr; Reed A. Christenson, all of Lincoln, Nebr.

[73] Assignee: J. A. Woollam Co., Lincoln, Nebr.

[21] Appl. No.: 947,430

[22] Filed: Sep. 18, 1992

[51] Int. Cl.$^5$ .................. G01J 3/447; G01N 21/21
[52] U.S. Cl. .................................. 356/328; 356/369
[58] Field of Search ............... 356/367, 364, 369, 300, 356/319, 323, 326, 325, 328, 329, 331, 332, 334

[56] References Cited

U.S. PATENT DOCUMENTS

| | | | |
|---|---|---|---|
| 2,837,959 | 6/1958 | Saunderson et al. | 356/329 |
| 3,846,024 | 11/1974 | Turner | 356/326 |
| 4,227,079 | 10/1980 | Dukes et al. | 356/326 |
| 4,571,074 | 2/1986 | Thevenon | 356/328 |
| 4,606,641 | 8/1986 | Yamada et al. | 356/369 |

FOREIGN PATENT DOCUMENTS

| | | | |
|---|---|---|---|
| 49822 | 3/1982 | Japan | 356/319 |
| 8300257 | 1/1983 | WIPO | 356/326 |

*Primary Examiner*—F. L. Evans
*Attorney, Agent, or Firm*—Vincent L. Carney

[57] ABSTRACT

To sense characteristics of a sample, an ellipsometer includes a pivotal diffraction grating positioned to receive white light from the analyzer without further focusing of the light after the light leaves the sample. The diffraction grating is focused on the sensor at a predetermined angle with a precision of at least plus or minus one-half degree using an alignment-sensing means positioned between the analyzer and diffraction grating. The sensor includes an aperture through which the incident beam of light is transmitted, light-sensitive areas on opposite sides of said sensor and a comparator for comparing the signal from said light-sensitive areas. Equality of the light from the light-sensitive areas indicates that the incident beam of light is perpendicular to the diffraction grating. A second diffraction grating and a second sensing means may receive the specularly reflected white light from a first diffraction grating and reflect it to another diffraction grating to investigate another spectrum of light. A spectroscopic ellipsometer uses a stacked photodiode in which the first photodiode and second photodiode have overlapping spectral ranges.

15 Claims, 5 Drawing Sheets

ELLIPSOMETER

BACKGROUND OF THE INVENTION

This invention relates to spectroscopic ellipsometers and methods of ellipsometry.

In one class of spectroscopic ellipsometer, an optical system focuses light from a light source through a monochromator, a polarization-state generator, a sample and an analyzer to determine the polarization state of the light caused by the reflection from the sample. The resulting light pattern is detected by a photodetector to provide an analog electrical signal that indicates the polarization state of the light. In some ellipsometers, the analog electrical signal is converted to a digital signal. The position of the sample and detector is usually manually adjustable to obtain the proper angle of impinging light.

In a prior art type of spectroscopic ellipsometer of this class, the optical system includes one or more lens systems, mirror systems or a combination of the two types of systems to focus the light from the light source through a monochromator slit onto the diffraction grating. The grating and mirrors are prealigned and calibrated in the monochromator. The light reflected from the sample, after being affected by an analyzer, is detected by a photomultiplier tube, and then converted to an electrical signal. The electrical signal is directly digitized by an analog-to-digital converter.

The prior art systems of this type have the disadvantages of being unduly complex, expensive and time-consuming to adjust. Part of the complexity occurs because photomultiplier tubes are used to obtain increased sensitivity instead of using diode detectors. However, simple, inexpensive diode detectors usually have too poor a signal-to-noise ratio with the intensity of light provided by the prior art spectroscopic ellipsometers.

SUMMARY OF THE INVENTION

Accordingly, it is an object of the invention to provide an improved spectroscopic ellipsometer and improved spectroscopic ellipsometry techniques.

It is a further object of the invention to provide a less complicated optical system for transmitting light to the diffraction grating.

It is a further object of the invention to provide a system that provides improved light throughput and that improves the signal-to-noise ratio.

It is a still further object of the invention to provide a technique permitting the use of diodes in a spectroscopic ellipsometer with adequate sensitivity.

In accordance with the above and further objects of the invention, light from a light source is collimated and transmitted through a polarization-state generator, a sample and an analyzer. In one embodiment, the light leaving the analyzer is white collimated light, and this light is applied to a diffraction grating without further focusing.

In this embodiment, light reflected from the diffraction grating is sensed by a photodiode array. The diffraction grating is aligned so that the incident collimated light is at a known angle with respect to the grating. This is achieved by a photodetector arrangement that receives the white light specularly reflected from the diffraction grating, such that it senses any deviation from the desired angular relationship between the incident collimated light and the grating. The diffraction grating reflects a predetermined spectrum of light to the photodiode array.

In another embodiment, a pivotal diffraction grating is aligned with the collimated incident light and then repositioned to refocus the diffracted light by turning the diffraction grating at an angle. In one variation of this embodiment, the white light spectrum from the diffraction grating is focused on an additional diffraction grating. A first photodetector arrangement may derive a spectrum from the first diffraction grating and a second sensor from the second grating, thus permitting either a second spectrum or more points in a portion of the spectrum sensed by the first array.

In still another embodiment, a monochromator applies a single wavelength of light to the polarization-state generator, sample and analyzer and that light is sensed by a stacked diode sensor. Thus, the stacked detector can be used to sense two different spectral ranges of light without physically switching detectors.

From the above description, it can be understood that the spectroscopic ellipsometer of this invention has several advantages, such as: (1) it is simple, inexpensive and relatively easy to operate compared to other spectroscopic ellipsometers with the same capability; (2) it is relatively sensitive for a spectroscopic ellipsometer using inexpensive detectors; and (3) it is relatively easy to adjust the diffraction grating for precise reflection onto the photodiode array.

DETAILED DESCRIPTION

Figure 1:
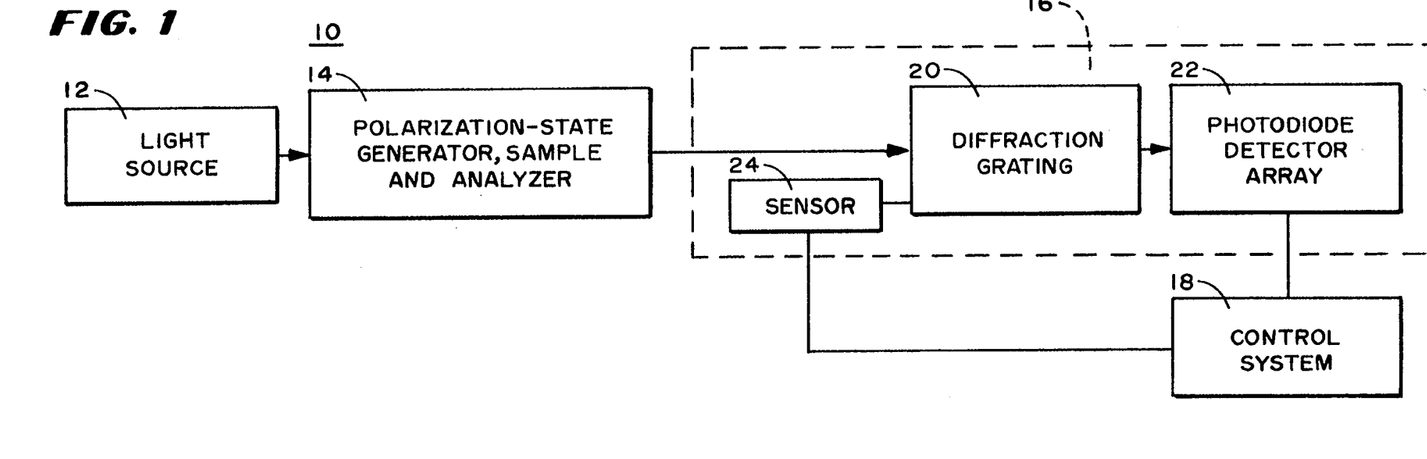
FIG. 1 is a block diagram of an embodiment of spectroscopic ellipsometer.

In FIG. 1, there is shown a block diagram of a spectroscopic ellipsometer 10 in accordance with an embodiment of the invention having a light source 12, a polarization-state generator, sample and analyzer 14, a detection system 16 and a control system 18 arranged with respect to each other so that: (1) the light source 12 transmits white light to the polarization-state generator, sample and analyzer 14; (2) the polarization-state generator, sample and analyzer 14 sets a polarization state of the light transmitted to the sample, which changes the polarization state in the light reflected from the sample and converts the light reflected from the sample into a time varying pattern of light intensity; and (3) the detection system 16 detects the light to provide an electrical signal indicating the change in the polarization due to reflection from the sample for transmission to the control system 18 as described in the literature. In this specification, the word "sample" is intended to cover any type of sample or container for a sample or support for a sample.

This light from the polarization-state generator, sample and analyzer 14 is processed in the detection system 16 to supply a spectrum of different wavelengths of light and that spectrum of different wavelengths of light is converted to electrical signals that are applied to the control system 18 for determination of the characteristics of the sample and indication of them to a user. The control system 18 is also capable of certain control functions in some embodiments of the invention and may be electrically connected to the detection system 16 or to the polarization-state generator, sample and analyzer 14 or light source 12 for that purpose. It may include any standard microprocessor, and the control system 18 is not part of the invention except insofar as it performs standard operations in an ellipsometer.

The detection system 16 includes a diffraction grating 20, a photodiode detector array 22 and a sensor 24. Commonly, the ellipsometer must be repositioned to sense the characteristics of the sample. Under some circumstances, it is necessary to align the diffraction grating 20 with the incident beam of light after the repositioning, and failure to do so reproduceably may result in an erroneous measurement. The sensor 24 and diffraction grating 20 are arranged with respect to each other to conveniently and precisely permit alignment of the diffraction grating 20 with respect to the light entering it and with respect to the photodiode detector array 22.

In constructing the detection system 16, the photodiode detector array 22 is aligned with the diffraction grating 20 so that, when the light is at a predetermined angle to the diffraction grating 20, the photodiode detector array 22 receives a spectrum of light useful in ellipsometry.

The ellipsometer 10 is spectrally calibrated at the factory. For such spectral calibration, light is supplied from a commercially obtained monochromator system, and the photodiode array is positioned so that, with the light from the monochromator incident at a predetermined angle on the diffraction grating, the photodetectors are receiving a spectrum of light in accordance with the design specifications. This calibration is necessary because the diffraction grating must position the spectrum of light on different photodiode elements in the photodiode array with sufficient precision to permit accurate resolution of the different wavelengths of light. The incident beam should be within 0.5 degrees from the predetermined angle (with respect to the diffraction grating) to achieve a reproduceable spectral shift and in the preferred embodiment is 0.02 degrees.

To obtain adequate alignment, the diffraction grating 20 is turned toward the source of light from the polarization-state generator, sample and analyzer 14. The sensor 24 senses the specularly reflected white light from the diffraction grating 20 and detects light reflected at an incorrect angle to indicate failure to align the diffraction grating 20. For example, four photodetectors precisely positioned and adjacent to each other can be used to indicate the relative light flux on each side of the sensor and thus indicate alignment.

In the preferred embodiment, the sensor 24 is a quadrant sensor, model SD225-23-21-040 manufactured and sold by Silican Detector Corporation, 1240 Avenida Acasco, Camarillo, Calif. 93010, U.S.A. It includes a central opening through which a beam of light may pass, with light-sensitive quadrants on four sides of the opening and provides four electrical signals, one from each quadrant of its light-sensitive surface. When those signals are all equal, the diffraction grating 20 is directly aligned at a predetermined angle with respect to the incident collimated light.

Figure 2:
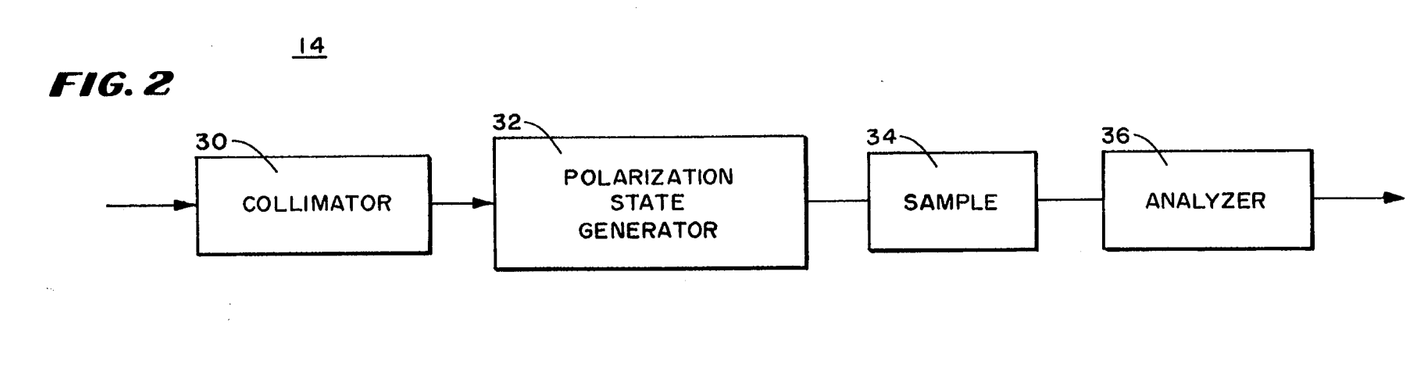
FIG. 2 is a block diagram of a portion of the spectroscopic ellipsometer of FIG. 1.

In FIG. 2, there is shown a block diagram of the polarization-state generator, sample and analyzer 14 having a collimator 30, a polarization-state generator 32, a sample 34 and an analyzer 36. The collimator 30 receives light directly from the light source without an intermediate monochromator and collimates it. This reduces the complexity of the apparatus and enables a higher intensity of light from the same light source to be applied by the collimator 30 to the polarization-state generator 32 located between the collimator 30 and the sample 34. In the preferred embodiment, the polarization-state generator 32 includes a fixed polarizer and a contiuously rotating polarizer. The analyzer 36 consists of a fixed polarizer.

The polarization-state generator 32 is positioned to transmit light to the sample 34 where it is affected by the sample therein. Light reflected from the sample has its polarization state changed, and the changed light is reflected to the analyzer 36, which in the embodiment of FIG. 2 is a fixed polarizer. The light transmitted from the analyzer 36 to the detection system 16 (FIG. 1) is totally polarized, but indicates the polarization state created by reflection from the sample with periodic intensity changes in the light as a function of time. The period of the intensity changes is related to the frequency of modulation applied in the polarization state generator.

Although one configuration of polarization-state generator, sample and analyzer 14 has been described in some detail, many other combinations and arrangements of the individual elements are possible with equally beneficial results. Such devices are described in the literature and can incorporate different arrangements of rotating and stationary polarizers suitable for use in this invention.

Figure 3:
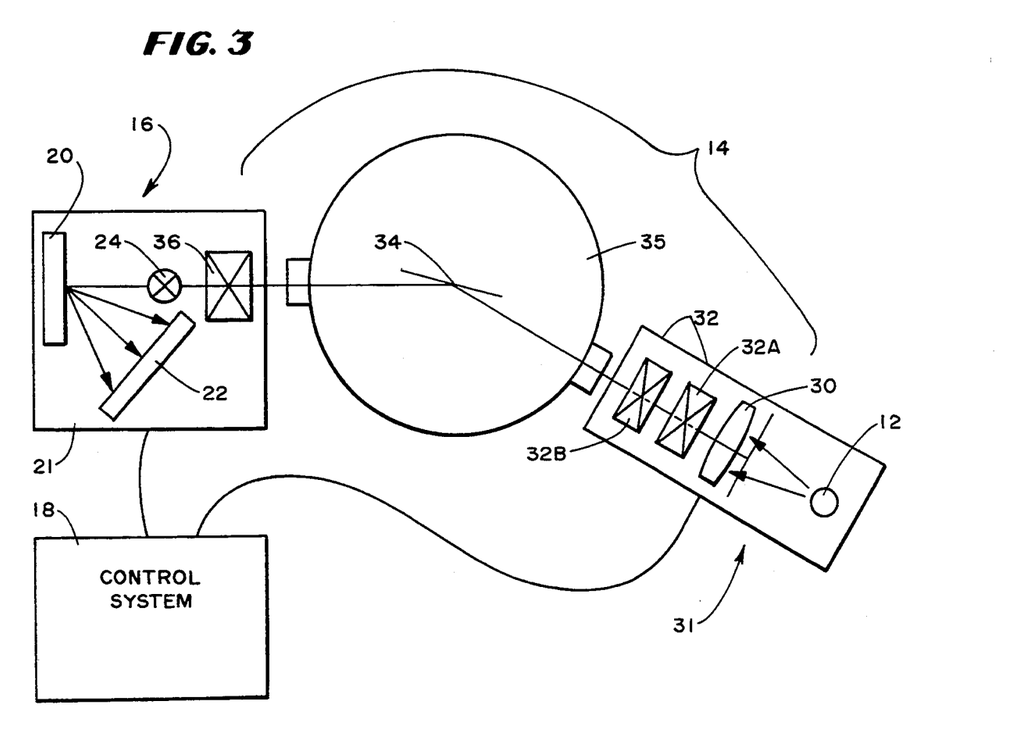
FIG. 3 is a schematic drawing of an analyzing and detecting portion of the spectroscopic ellipsometer of FIG. 1.

In FIG. 3, there is shown a schematic drawing of the ellipsometer 10 showing the light source 12, the polarization-state generator, sample and analyzer 14, the detector system 16 and the control system 18 arranged in a manner indicating how they may be packaged together to be readily moved to a specific site. For example, in FIG. 3, a sample 34 is not able to be readily moved to the ellipsometer and is measured at its site.

In this circumstance, a first housing 31 includes the light source 12, a collimator 30 and the polarization-state generator 32, aligned to transmit light to the sample 34, and a second housing 21 includes the analyzer 36, a sensor 24, the diffraction grating 20 and a photodiode sensing array 22. These two housings are positioned sufficiently near the location 35 of the sample 34 located so that light from the first housing 31 may be transmited to the sample 34 and light reflected from the sample 34 may be collected by the detector system 16 which generates electrical signals and supplies them to the control system 18.

The polarization-state generator 32, in this embodiment, includes a fixed polarizer 32A and a continuously rotating polarizer 32B so that the light emitted by the light source 12 is collimated by a lens 30 and passed through the polarization-state generator 32 before reaching the sample 34. In the preferred embodiment, the light source 12 is a source of white light and may be a xenon arc lamp.

The second housing 21 is adapted to have its operative elements aligned with the reflected light from the sample 34 so that the light passes through the analyzer 36 and an aperture in the sensor 24 to the diffraction grating 20. These operative elements are prealigned at the factory using a commercially obtained monochromator until the incident light is at a predetermined angle to the diffraction grating 20, and at that time, the desired spectrum of light is applied to the photodetectors in the photodiode array 22.

To align the second housing 21, the sensor 24 is a quadrant sensor with a one millimeter center aperture. The light beam passing through that aperture is specularly reflected from the diffraction grating 20, and when close to normal, the light reflects onto the quadrants of the quadrant sensor 24.

If more light is reflected on one quadrant than another, a signal is provided indicating that the second housing 21 should be adjusted. When the light is equal from all quadrants, the housing 21 and its operative elements, the analyzer 36, diffraction grating 20 and photodiode array 22 are all in the proper alignment. The balance can be determined by comparison: (1) by hand such as with a null bridge or meter or other instrument; or (2) automatically such as by comparators within the control system 18 as in the preferred embodiment.

Figure 4:
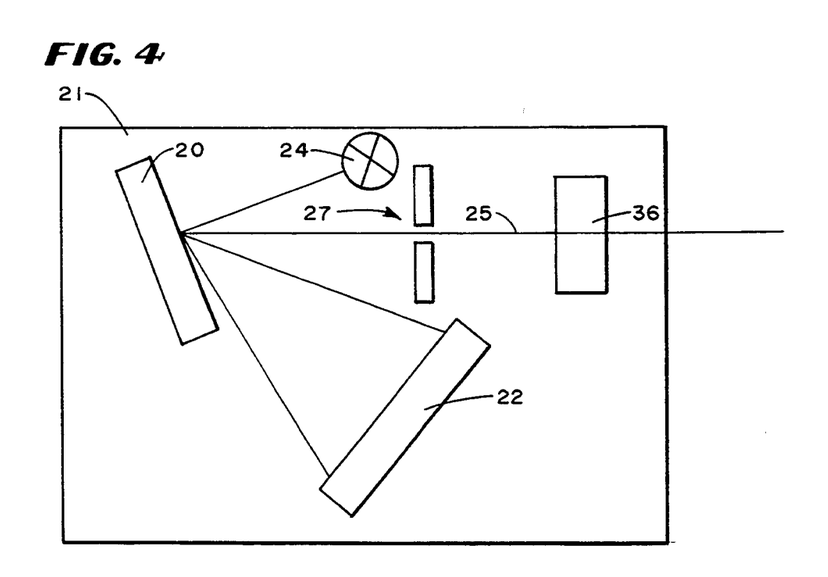
FIG. 4 is a schematic diagram of another embodiment of a portion of the analyzing and detecting portion of the spectroscopic ellipsometer of FIG. 1.

In FIG. 4, there is shown another embodiment of the second housing 21 that is the same as the embodiment of FIG. 3 except that the diffraction grating 20 is at a slight angle, such as for example, 10 degrees to the incident light beam 25, the quadrant sensor 24 is positioned a short distance from the incident light beam 25 so that it receives first order specularly reflected light and a separate aperture plate 27 is positioned so that the light beam 25 is blocked except for that passing through an aperture in the aperture plate 27. The quadrant sensor 24 is used in the same manner as described in connection with FIG. 3 to align the housing 21 so the diffraction grating is at the predetermined angle at which the first order specular light is directed to the sensor 24 and the diffracted light is reflected to the photodiode sensing array 22 as these units are positioned in the housing in accordance with the design of the ellipsometer.

Figure 5:
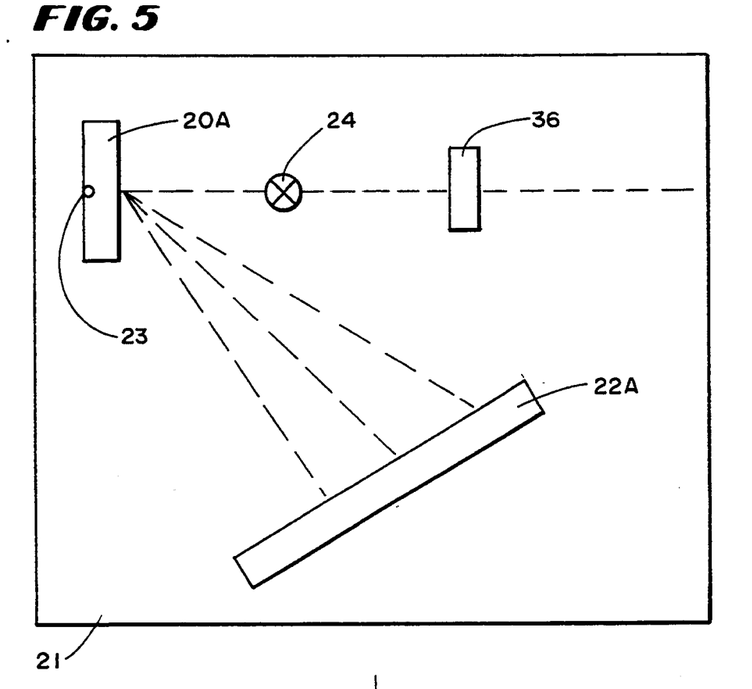
FIG. 5 is a schematic drawing of still another embodiment of an analyzing and detecting portion of the spectroscopic ellipsometer of FIG. 1.

In FIG. 5, there is shown still another embodiment of the second housing 21 having a diffraction grating 20A pivotable about a pivot point 23 to align it with the diode array 22A. This arrangement can receive incident light passing through the analyzer 36 and quadrant sensor 24 at different angles (with respect to the diffraction grating) to provide different wavelength ranges to the diode array 22A. The diode array 22A can be aligned by rotating the diffraction grating 20A and recording the location where the specularly reflected white light is observed in the photodiode array 22A. As an alternative, the diffraction grating 20A may remain fixed and the diode array 22A may be slidable, or both mechanisms may be provided.

Figure 6:
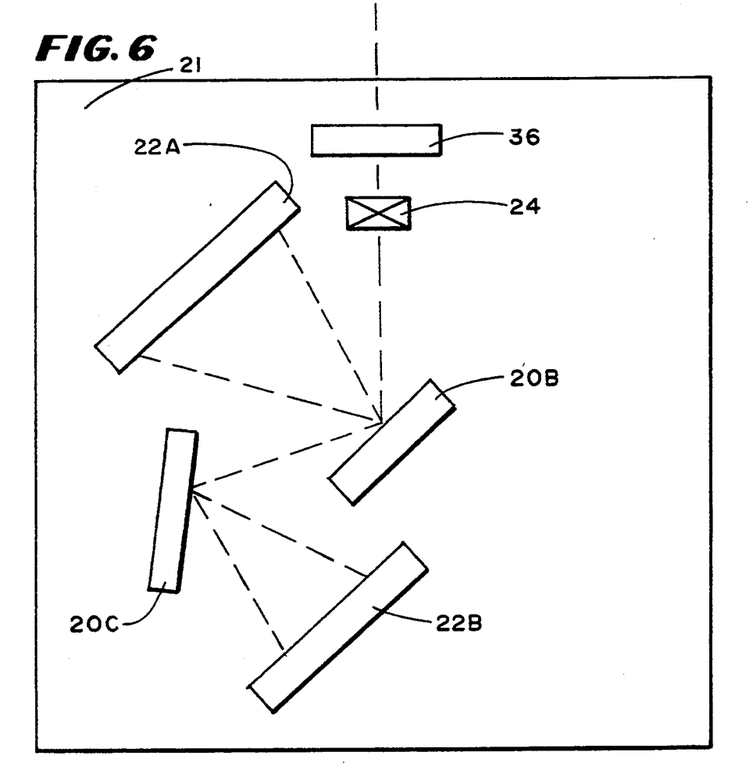
FIG. 6 is a schematic drawing of still another embodiment of the analyzing and detecting portion of the spectroscopic ellipsometer of FIG. 1.

In FIG. 6, there is shown still another embodiment within the second housing 21 including the analyzer 36 and quadrant sensor 24 arranged in the same manner as in the embodiments of FIGS. 3 and 5. In the embodiment of FIG. 6, a grating 20B reflects a spectrum onto the diode array 22A and its specularly reflected white light on another grating 20C that focuses another spectrum on still another photodiode array 22B. In this manner, more areas of the spectrum can be analyzed from the positioning of the two different photodiode arrays 22A and 22B.

With this arrangement, the two diffraction gratings can each provide a spectrum from a different range, such as for example, one providing a range from 0.25 to 0.5 micron wavelength and the second covering a range of between 0.5 to 1.0 microns in wavelength. This is useful because each grating has a limited useful spectral range and becomes inefficient outside of that range. Thus, using both spectrums avoids the need to substitute one grating for another when a different range is being explored.

Figure 7:
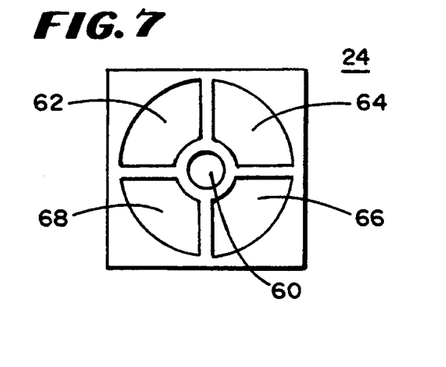
FIG. 7 is a plan view of a quadrant sensor usable in an embodiment of the invention.
Figure 8:
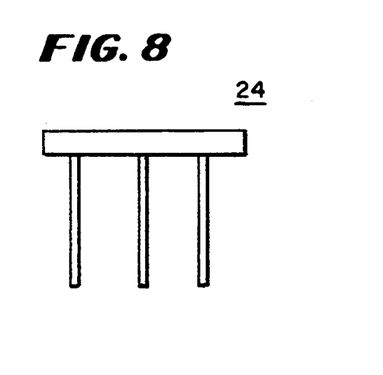
FIG. 8 is a side view of the quadrant sensor of FIG. 7.
Figure 9:
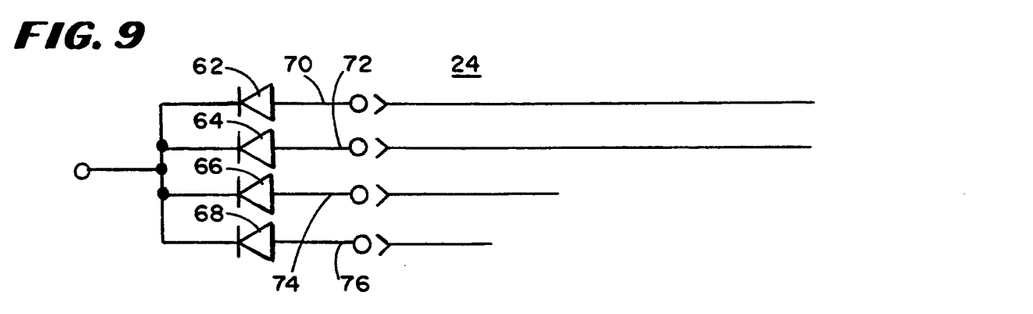
FIG. 9 is a schematic view of the quadrant sensor of FIG. 7.

In FIG. 7, FIG. 8 and FIG. 9, there are shown a plan view, a side view and a schematic view respectively of the quadrant sensor 24 having a central aperture 60, and four light-sensitive areas 62, 64, 66 and 68. The central aperture 60 is positioned to be aligned with the central axis of a beam of light. Each of the four light-sensitive areas forms a different one of the four quadrants of a circle with the aperture 60 as its center so that a beam of light with its center axis aligned with the aperture 60 overlaps equally in each of the four light-sensitive areas 62, 64, 66 and 68.

Each of the four light-sensitive areas 62, 64, 66 and 68 is represented by a different one of the diodes indicated by the same reference numbers in FIG. 7 and is connected to a different one of the conductors 70, 72, 74 and 76 respectively so that when the light is not reflected evenly back toward the sensor 24 from the diffraction grating 20, different amplitude signals are being applied to each of the conductors 70, 72, 74 and 76. The angle of the diffraction grating 20 is adjusted until the amplitude of the signals from the four light-sensitive quadrants 62, 64, 66 and 68 are the same. When the amplitudes of the signals from the four light-sensitive quadrants are the same, the incident light reflected from the grating is at the proper angle of incidence. In the preferred embodiment, the signals from the conductors 70–76 are applied to the analog-to digital converter 106 (FIG. 13) for comparison in the microprocessor 112.

Figure 10:
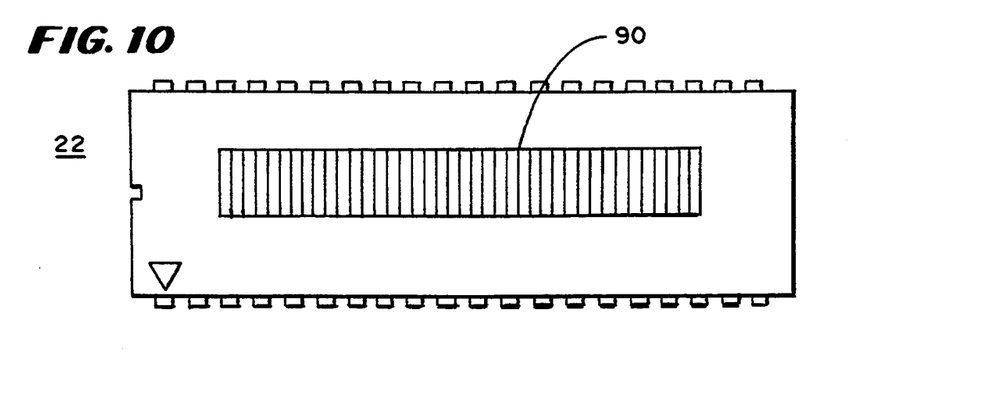
FIG. 10 is a plan view of an embodiment of detector usable in the embodiments of FIGS. 1-6.
Figure 11:
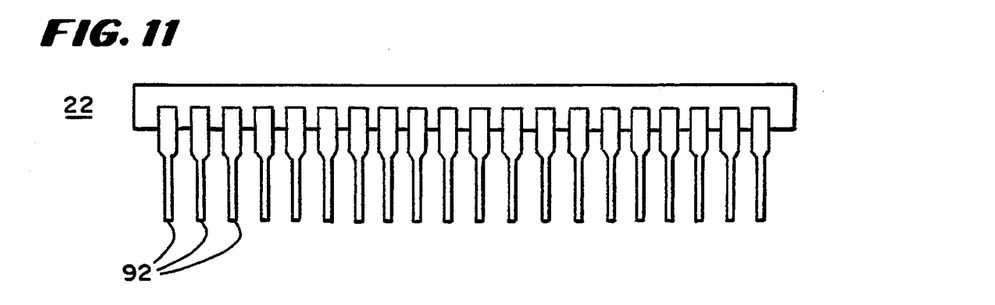
FIG. 11 is a plan view and side elevational sectional view respectively of the detector of FIG. 10.

In FIG. 10 and FIG. 11, there are shown a plan view and side elevational sectional view respectively of the photodiode array 22. In the preferred embodiment, this photodiode array is the type PDA38 sold by E. G. and G. Judson, 221 Commerce Drive, Montgomeryville, Pa. 18936, U.S.A. It includes an element having a plurality of photodiodes 90 each of which has its individual conductors shown generally at 92. The entire chip is approximately 15.2 millimeters wide, 51 millimeters long and 3 millimeters deep with 4.5 -millimeter long connecting leads spaced 2.54 millimeters center-to-center and being 0.48 millimeters wide. The active area of the photodiodes is approximately 3.8 square millimeters. This relatively small array requires careful alignment of the spectrum from the diffraction grating but is economical in use. Consequently, the diffraction grating should be able to direct light onto the photodiode array within plus or minus one degree and this requires precise alignment with respect to the incident light.

Figure 12:
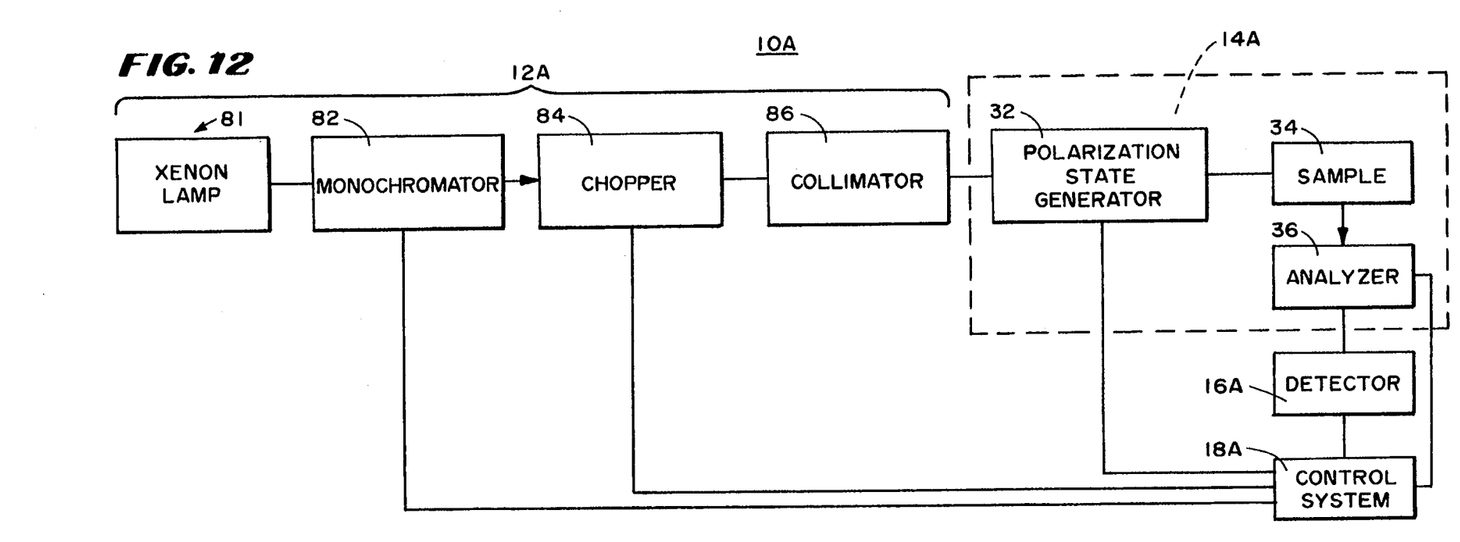
FIG. 12 is a block diagram of another embodiment of polarization-state generator, sample and analyzer usable in a spectroscopic ellipsometer.

In FIG. 12, there is shown a block diagram of another embodiment of ellipsometer 10A having a light source 12A, a polarization-state generator 32, a sample and analyzer 14A, a detector 16A and a control system 18A. In this embodiment, the light source 12A selects a frequency of the light from a xenon lamp, chops it, filters it, collimates it and transmits it to the polarization-state generator 32 and the sample and analyzer 14A. The light source uses a xenon lamp to take data in a range between 0.25 to 1.7 microns wavelength.

To provide a collimated beam of chopped light, the light source 12A includes a xenon lamp 81, a monochromator 82, a chopper 84, an order sorting filter and a collimater 86. The Xenon lamp 81 generates white light, one wavelength of which is selected by the monochromator 82 in a manner known in the art under the control of the control system 18A. This wavelength of light is chopped in the chopper 84 at a conventional chopping rate, filtered by the appropriate filter and transmitted through the collimator 86, which collimates it prior to transmitting it onto the polarization state generator, sample and analyzer 14A. With this embodiment, a conventional collimated chopped light is transmitted for later application, after polarization, to the sample.

The polarization-state generator 32 polarizes light and transmits it to the sample 34. Light is reflected from the sample 34 to the analyzer 36 that provides intensity fluctuations to the detector 16A representing the changes in polarization state caused by the sample 34. The light signal is transmitted to the detector 16A for conversion to electrical signals and the electrical signals are applied to the control system 18A for analysis in a conventional way.

The time varying light pattern from the analyzer 36 indicating the change in the polarization state of light caused by the sample 34 are applied to the detector 16A which converts the chopped light pulses to electrical signals for application to the control system 18A. In the preferred embodiment, the detector 16A is a two-color silicon photodiode indicated as a UV-Si/InGaAs-jA photodiode (silicon-indium gallium arsenide photodiode) having a silicon area of 0.58 centimeters (0.20 square centimeters) and an InGaAs area of 0.30 centimeters and sold by Electro-Optical Systems, Inc., Greenway Technology Park, 1000 Nutt Road, Phoenixville, Pa. 19460, U.S.A. The computer selectively connects one of the two silicon photodiodes in circuit with the control system 18A. In this circuit, one wavelength range of light is detected by the silicon level and the other passes through it (silicon is transparent in the near infrared) to the indium gallium arsenide level for detection. The computer selects which of the readouts is desired.

Figure 13:
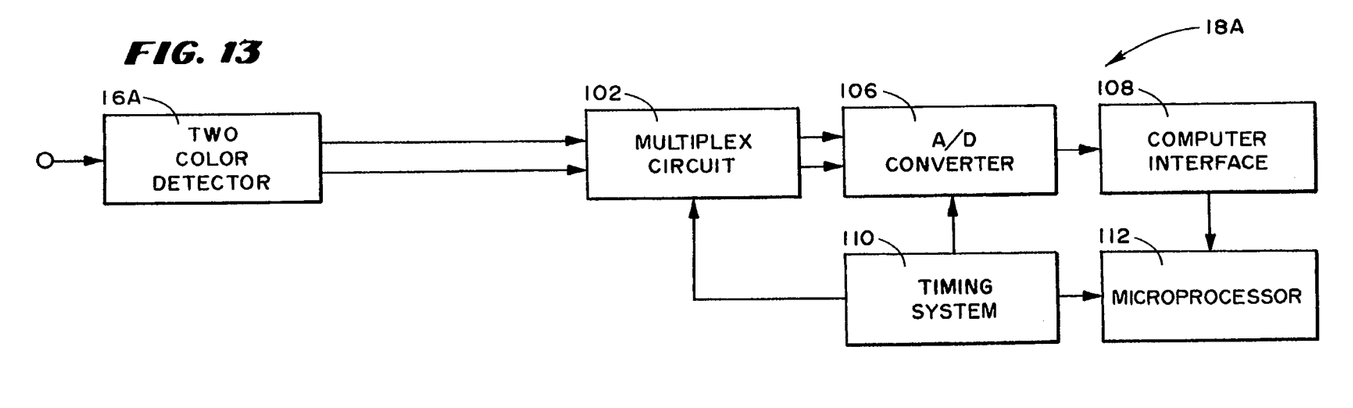
FIG. 13 is a block diagram of another detector system usable in a spectroscopic ellipsometer.

In FIG. 13, there is shown a block diagram of the detector 16A and control system 18A connected together to receive a light pattern, generate an electrical signal from the light pattern and provide information concerning the sample from it. For this purpose, the detector 16A is a two-color detector and the control system 18A includes a multiplex circuit 102, an A/D converter 106, a computer interface 108, a microprocessor 112 and a timing system 110.

With this arrangement, the wavelength of light from the two-color detector 100 is selected, the signal representing it is supplied as an analog electrical signal to the A/D converter 106 in the control system 18A. This signal is digitized in the A/D converter 106 and supplied to the computer interface 108 and then to the microprocessor 112 through the computer interface 108. These circuits operate under the control of the timing system 110. The timing system causes the A/D converter 106 to sample data and apply it to the microprocessor 112 through the computer interface 108 at a rate controlled by the timing system 110 to be faster than the chopping rate of the chopper 84.

In the preferred embodiment, a smooth overlap of the spectral range is obtained because the two diodes in the two-color detector overlap in response over a range of wavelengths. Using the xenon lamp with the two-color detector 100 allows spectral coverage from 0.25 microns to 1.7 microns without switching light sources or detector systems. If a quartz tungsten halogen lamp is used, data could not be obtained below approximately 0.4 microns and it would be necessary to change light sources to a xenon lamp to take data at these short wavelengths.

As can be understood from the above description, the spectroscopic ellipsometer of this invention has the advantage of being economical in construction, easy to operate and simple to calibrate. In one embodiment, it requires only the use of a simple diffraction grating, rather than a complex monochromator system, to obtain spectroscopic ellipsometric data.

While a preferred embodiment of the invention has been described in some detail, many variations and modifications of the preferred embodiment are possible in the light of the above teachings. Therefore, it is to be understood that, within the scope of the appended claims, the invention may be practiced other than as specifically described.

What is claimed is:

1. A spectroscopic ellipsometer adapted to sense characteristics of a sample comprising:
   a light source;
   a polarization-state generator;
   an analyzer; and
   a diffraction grating and a collimator positioned so that the diffraction grating receives collimated white light passing through the analyzer without further focusing after the light leaves the sample and transmits the white light to a detector; wherein the diffraction grating reflects incident light onto the detector at a predetermined angle with respect to a normal to the diffraction grating with a precision of at least plus or minus one-half degree.

2. A spectroscopic ellipsometer in accordance with claim 1 in which said diffraction grating is pivotable.

3. A spectroscopic ellipsometer in accordance with claim 1 further including:
   an alignment-sensing means for sensing an alignment of an incident beam of light from the analyzer to the surface of the diffraction grating;
   said alignment-sensing means including an aperture through which the incident beam of light is transmitted and an alignment light sensor having at least first and second light-sensitive areas on opposite sides of said alignment light sensor;
   means for comparing the signal from said light-sensitive areas;
   said alignment-sensing means being positioned between the analyzer and the diffraction grating whereby it receives light specularly reflected from the diffraction grating;

said alignment-sensing means being adapted to sense light specularly reflected from the diffraction grating, whereby an equality of the light from the light-sensitive areas indicates that the incident beam of light is aligned at a predetermined angle to the diffraction grating.

4. A spectroscopic ellipsometer in accordance with claim 3 further including a second diffraction grating and a second detector whereby specularly reflected white light from the first mentioned diffraction grating is reflected to the second diffraction grating.

5. A spectroscopic ellipsometer in accordance with claim 1 in which said sensor is a silicon diode array.

6. A spectroscopic ellipsometer in accordance with claim 1 in which the collimator is positioned to receive light from a light source and transmit it to the polarization-state generator without either divergence or convergence of the light by more than ten degrees between the collimator and the diffraction grating.

7. A spectroscopic ellipsometer in accordance with claim 1 in which the light is transmitted from the light source to the polarization-state generator without passing through a monochromator.

8. A spectroscopic ellipsometer comprising:
   a light source including a monochromator;
   a polarization-state generator;
   an analyzer; and
   a detector positioned so that light from a monochromator is transmitted through the polarization-state generator, reflected from a sample and transmitted through the analyzer to the detector;
   said detector including a stacked photodiode in which the light transmitted through a first photodiode impinges on a second photodiode, said photodiodes having partly overlapping spectral ranges.

9. A spectroscopic ellipsometer in accordance with claim 8 in which a spectrum covers a wavelength range between 0.25 to 1.7 microns.

10. A spectroscopic ellipsometer in accordance with claim 8 in which the light source includes a xenon lamp.

11. A method of aligning a diffraction grating with incident light comprising the steps of:
   transmitting the incident light through an aperture having light-sensitive areas on at least two of its sides to the diffraction grating; and
   sensing the light specularly reflected from the diffraction grating on the at least two adjacent light sensitive areas a known distance from the aperture: and
   adjusting the position of the diffraction grating until the light on said at least two light-sensitive areas is balanced.

12. A method of aligning a diffraction grating with incident light comprising the steps of:
   transmitting the incident light through an aperture to the diffraction grating;
   sensing light specularly reflected from the diffraction grating with a sensing means having at least two adjacent light sensitive areas a known distance from the aperture; and
   adjusting the position of the diffraction grating until the light on said at least two light-sensitive areas is balanced.

13. A method of spectroscopic analysis comprising the steps of:
   transmitting collimated light through a polarization-state generator;
   reflecting the collimated light from a sample;
   transmitting the reflected light to an analyzer; and
   transmitting the light from the analyzer to a diffraction grating without further focusing after the light is reflected from the sample.

14. A method of spectroscopic analysis in accordance with claim 13 further comprising the steps of:
   transmitting one spectrum of light from said diffraction grating to a first detector and reflecting a second spectrum of light to a second diffraction grating, wherein said second spectrum includes at least a white light band; and
   transmitting the second spectrum of diffracted light from the second diffraction grating to a second detector.

15. A method of performing ellipsometry comprising the steps of:
   transmitting monochromatic light through a polarization-state generator to a sample; and
   receiving reflected light from the sample after it passes through an analyzer onto a two-stacked photodiodes, whereby two separate wavelength ranges of light may be received, said wavelength ranges overlapping.

* * * * *